United States Patent [19]
Haight et al.

[11] Patent Number: 5,672,706
[45] Date of Patent: Sep. 30, 1997

[54] PROCESS FOR THE PREPARATION OF A SUBSTITUTED 2,5-DIAMINO-3-HYDROXYHEXANE

[75] Inventors: Anthony R. Haight, Mundelein; Owen J. Goodmonson, Buffalo Grove; Shyamal L Parekh, Gurnee; Timothy A. Robbins, Waukegan; Lou S. Seif, Buffalo Grove, all of Ill.

[73] Assignee: Abbott Laboratories, Abbott Park, Ill.

[21] Appl. No.: 633,605

[22] Filed: Apr. 17, 1996

Related U.S. Application Data

[63] Continuation of Ser. No. 283,109, Jul. 29, 1994, abandoned.

[51] Int. Cl.[6] ............ C07D 209/44; C07D 221/14; C07C 213/00; C07C 209/68
[52] U.S. Cl. ............ 546/99; 548/509; 564/357; 564/358
[58] Field of Search ............ 564/357, 358; 546/99; 548/509

[56] References Cited

U.S. PATENT DOCUMENTS 4,360,684  11/1982  Cvetovich et al. ............ 549/291

FOREIGN PATENT DOCUMENTS 486948  5/1992  European Pat. Off. .
WO94/14436  7/1994  WIPO .

OTHER PUBLICATIONS

D. Melillo, et al., J. Org. Chem. 51 1498 (1986) Publication month not provided.
M. Freifelder, J. Org. Chem. 29 2895 (1964) Publication month not provided.
C. Koelsch, et al., J. Org. Chem. 26 1104 (1961) Publication month not provided.
E. Wenkert, et al., J. Org. Chem. 33 747 (1968) Publication month not provided.
N. Albertson, J. Am. Chem. Soc. 74 249 (1952) Publication month not provided.
G. Stork, et al., J. Am. Chem. Soc. 89 5459 (1967) Publication month not provided.
D. Claremon, et al., Tet. Lett. 5417 (1985) Publication month not provided.
A. Barco, et al., Syn. Commun. 8 219 (1978) Publication month not provided.

(List continued on next page.)

Primary Examiner—Mukund J. Shah
Assistant Examiner—King Lit Wong
Attorney, Agent, or Firm—Steven R. Crowley

[57] ABSTRACT

A process is disclosed for the preparation of the substantially pure compound of the formula:

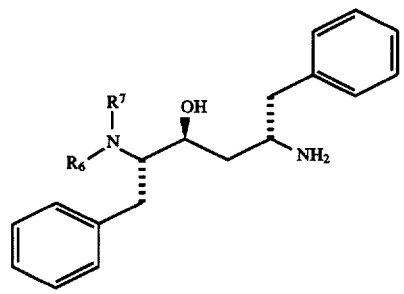

comprising catalytic hydrogenation of a compound of the formula:

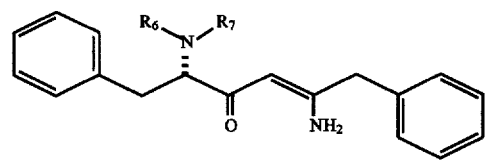

wherein $R_6$ and $R_7$ are independently selected from

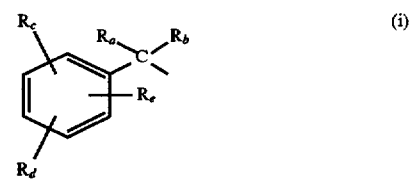

(i)

wherein $R_a$ and $R_b$ are independently selected from hydrogen, loweralkyl and phenyl and $R_c$, $R_d$ and $R_e$ are independently selected from hydrogen, loweralkyl, trifluoromethyl, alkoxy, halo and phenyl; and

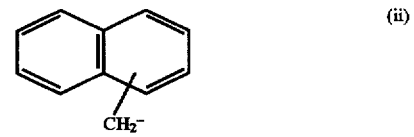

(ii)

wherein the naphthyl ring is unsubstituted or substituted with one, two or three substitutents independently selected from loweralkyl, trifluoromethyl, alkoxy and halo; or $R_6$ and $R_7$ taken together with the nitrogen atom to which they are bonded are

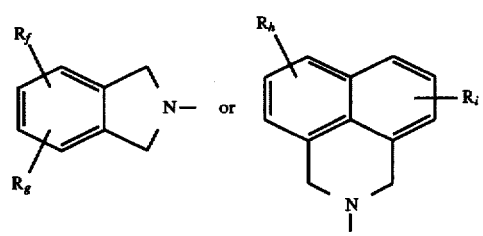

wherein $R_f$, $R_g$, $R_h$ and $R_i$ are independently selected from hydrogen, loweralkyl, alkoxy, halogen and trifluoromethyl; or an acid addition salt thereof.

15 Claims, No Drawings

OTHER PUBLICATIONS

T. Moriya, et al., J. Org. Chem. 47 94 (1982) Publication month not provided.

H. Ishibashi, et al., Chem. Pharm. Bull 33 4593 (1985) Publication month not provided.

J. Martin, et al., J. Org. Chem. 31 943 (1966) Publication month not provided.

J. Greenhill, et al., JCS Perkin I 588 (1975) Publication month not provided.

J. Greenhill, et al., Chem. Soc. Rev. 6 277 (1977) Publication month not provided.

C. Skotsch, et al., Synthesis 449 (1979) Publication month not provided.

A. Ghosh, et al., J. Org. Chem. 58 1025 (1993) Publication month not provided.

PROCESS FOR THE PREPARATION OF A SUBSTITUTED 2,5-DIAMINO-3-HYDROXYHEXANE

This is a continuation of U.S. patent application Ser. No. 08/283,109, filed Jul. 29, 1994 now abandoned.

TECHNICAL FIELD

The present invention relates to intermediates and processes which are useful for the preparation of a substituted 2,5-diamino-3-hydroxyhexane.

BACKGROUND OF THE INVENTION

Compounds which are inhibitors of HIV protease are useful for inhibiting HIV protease in vitro and in vive and are useful for inhibiting an HIV infection. Certain HIV protease inhibitors comprise a moiety which is a substituted 2,5-diamino-3-hydroxyhexane. HIV protease inhibitors of particular interest are compounds of the formula 1:

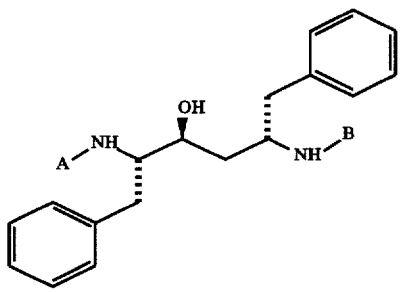

wherein A is $R_2NHCH(R_1)C(O)$- and B is $R_{2a}$ or wherein A is $R_{2a}$ and B is $R_2NHCH(R_1)C(O)$- wherein $R_1$ is loweralkyl and $R_2$ and $R_{2a}$ are independently selected from $-C(O)-R_3-R_4$ wherein at each occurrence $R_3$ is independently selected from O, S and $-N(R_5)$- wherein $R_5$ is hydrogen or loweralkyl and at each occurrence $R_4$ is independently selected from heterocyclic or (heterocyclic)alkyl; or a pharmaceutically acceptable salt, prodrug or ester thereof. Compounds of formula 1 are disclosed in European Patent Application No. EP0486948, published May 27, 1992.

A preferred HIV protease inhibitor of formula 1 is a compound of formula 2a:

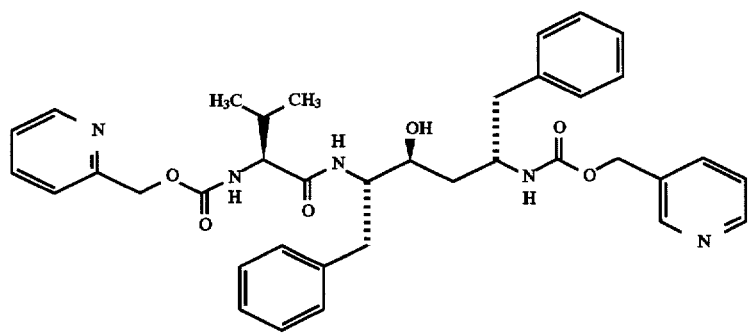

or a pharmaceutically acceptable salt, prodrug or ester thereof.

Another preferred HIV protease inhibitor of formula 1 is a compound of formula 2b:

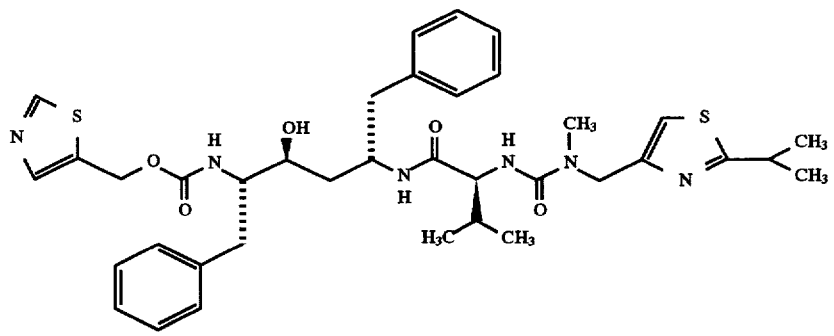

The compound of formula 2b is disclosed in PCT Patent Application No. WO94/14436, published Jul. 7, 1994, which is hereby incorporated herein by reference.

An intermediate which is especially useful for preparing compounds of the formula 1 and 2 is a substantially pure compound of the formula 3:

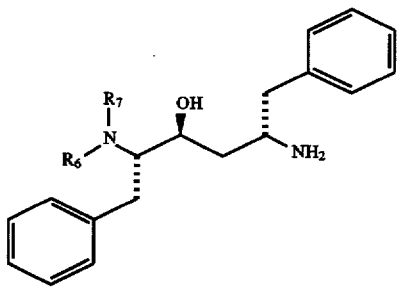

wherein $R_6$ and $R_7$ are independently selected from an N-protecting group; or an acid addition salt thereof. Preferred N-protecting groups $R_6$ and $R_7$ are independently selected from

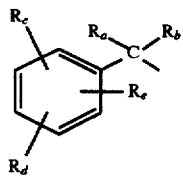

(i)

wherein $R_a$ and $R_b$ are independently selected from hydrogen, loweralkyl and phenyl and $R_c$, $R_d$ and $R_e$ are independently selected from hydrogen, loweralkyl, trifluoromethyl, alkoxy, halo and phenyl; and

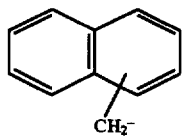

(ii)

wherein the naphthyl ring is unsubstituted or substituted with one, two or three substitutents independently selected from loweralkyl, trifluoromethyl, alkoxy and halo.

Alternatively, $R_6$ and $R_7$ taken together with the nitrogen atom to which they are bonded are

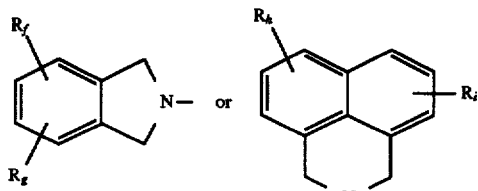

wherein $R_f$, $R_g$, $R_h$ and $R_i$ are independently selected from hydrogen, loweralkyl, alkoxy, halogen and trifluoromethyl.

More preferred N-protecting groups $R_6$ and $R_7$ are those wherein $R_6$ and $R_7$ are independently selected from benzyl and substituted benzyl wherein the phenyl ring of the benzyl group is substituted with one, two or three substituents independently selected from loweralkyl, trifluoromethyl, alkoxy, halo and phenyl. The most preferred N-protecting groups $R_6$ and $R_7$ are those wherein $R_6$ and $R_7$ are each benzyl.

Preferred intermediates of the formula 3 are the compounds wherein $R_6$ and $R_7$ are each benzyl or substituted benzyl wherein the phenyl ring of the benzyl group is substituted with one, two or three substituents independently selected from loweralkyl, trifluoromethyl, alkoxy, halo and phenyl. More preferred intermediates of the formula 3 are the compounds wherein $R_6$ and $R_7$ are benzyl.

DISCLOSURE OF THE INVENTION

The present invention relates to a process for the preparation of a substantially pure compound of the formula 3. A key intermediate in the process of the present invention is a substantially pure enaminoketone compound of the formula 4:

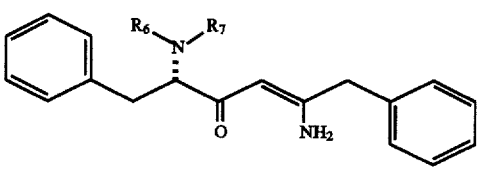

wherein $R_6$ and $R_7$ independently selected from an N-protecting group; or an acid addition salt thereof. Preferred N-protecting groups $R_6$ and $R_7$ are independently selected from

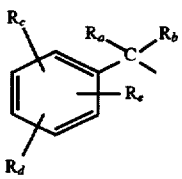

(i)

wherein $R_a$ and $R_b$ are independently selected from hydrogen; loweralkyl and phenyl and $R_c$, $R_d$ and $R_e$ are independently selected from hydrogen, loweralkyl, trifluoromethyl, alkoxy, halo and phenyl; and

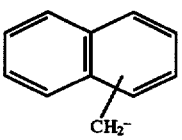

(ii)

wherein the naphthyl ring is unsubstituted or substituted with one, two or three substitutents independently selected from loweralkyl, trifluoromethyl, alkoxy and halo.

Alternatively, $R_6$ and $R_7$ taken together with the nitrogen atom to which they are bonded are

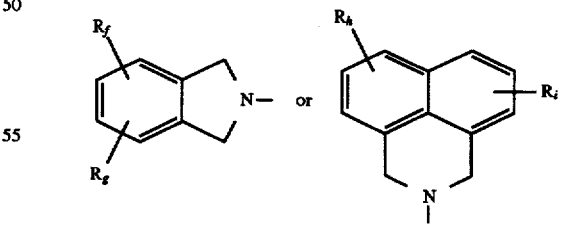

wherein $R_f$, $R_g$, $R_h$ and $R_i$ are independently selected from hydrogen, loweralkyl, alkoxy, halogen and trifluoromethyl.

Preferred intermediates of the formula 4 are the compounds wherein $R_6$ and $R_7$ are each benzyl or substituted benzyl wherein the phenyl ring of the benzyl group is substituted with one, two or three substituents independently selected from loweralkyl, trifluoromethyl, alkoxy, halo and phenyl. More preferred intermediates of the formula 4 are the compounds wherein $R_6$ and $R_7$ are benzyl. Compound 4 and a process for its preparation are disclosed in U.S. patent application Ser. No. 141,795, filed Oct. 22, 1993, which is hereby incorporated herein by reference.

A process for the preparation of 3 from 4 involves catalytic hydrogenation of 3 in a solvent comprising (1) a protic solvent, (2) an ethereal solvent or (3) a mixture of a protic solvent and a hydrocarbon solvent in the presence of an acid.

In particular, the process comprises dissolving compound 3 in an appropriate solvent, adding the acid, then adding the hydrogenation catalyst and, finally, pressurizing the reaction vessel with hydrogen gas.

A preferred solvent for the process is (1) a protic solvent such as an alcohol (for example, isopropanol, methanol, ethanol, t-butanol, sec-butanol, n-butanol or propanol and the like), (2) an ethereal solvent such as dimethoxyethane, methyl-t-butyl ether or dioxane and the like or (3) a mixture of a protic solvent and a hydrocarbon solvent (for example, pentane, hexane, heptane or toluene and the like). A most preferred solvent is ethanol.

A preferred acid is an inorganic acid (for example, HCl, HBr, sulfuric acid, phosphoric acid, perchloric acid, chlorosulfonic acid, fluorosulfonic acid, $Me_3SiOSO_3H$ and the like) or an organic acid selected from (i) $R_8$-COOH wherein $R_8$ is loweralkyl, haloalkyl, phenyl or halophenyl, (ii) $R_9$-$SO_3H$ wherein $R_9$ is loweralkyl, haloalkyl, phenyl, loweralkyl-substituted phenyl, halophenyl or naphthyl and (iii) $R_{10}$-$PO_3H_2$ wherein $R_{10}$ is loweralkyl or phenyl; or a combination of said acids.

Examples of acids $R_8$-COOH include acetic acid, propionic acid, trifluoroacetic acid, trichloroacetic acid, dichloroacetic acid, difluoroacetic acid, benzoic acid and pentafluorobenzoic acid. Examples of acids $R_9$-$SO_3H$ include methanesulfonic acid, ethanesulfonic acid, trifluoromethanesulfonic acid, phenylsulfonic acid and p-toluenesulfonic acid. Examples of acids $R_{10}$-$PO_3H_2$ include methylphosphonic acid, ethylphosphonic acid and phenylphosphonic acid.

A most preferred acid for the process of this invention is methanesulfonic acid or sulfuric acid.

A preferred amount of the acid is from about 2 molar equivalents to about 4 molar equivalents (based on the enaminoketone). A most preferred amount of the acid is from about 3 molar equivalents to about 4 molar equivalents.

A preferred hydrogenation catalyst is a platinum catalyst (including, platinum black or platinum oxide and the like). Preferably, the catalyst is supported on a support such as carbon, alumina, graphite, sulfided carbon, polyethyleneimine/$SiO_2$ (Royer, et al., J. Org. Chem. 45 2268 (1980)) or aminopolysiloxane (for example, Deloxan® AP II, available from Degussa, 65 Challenger Road, Ridgefield Park, N.J. 07660) and the like. Platinum on carbon can also be doped with Pd, Ru, Re or Rh. A most preferred catalyst is 5% platinum on carbon or 5% platinum on aminopolysiloxane.

The hydrogenation process is preferably carried out at a hydrogen pressure from about 60 psi to about 1000 psi. A most preferred hydrogen pressure is from about 250 psi to about 1000 psi.

The term "loweralkyl" as used herein refers to straight or branched chain alkyl radicals containing from 1 to 6 carbon atoms including, but not limited to, methyl, ethyl, n-propyl, iso-propyl, n-butyl, iso-butyl, sec-butyl, n-pentyl, 1-methylbutyl, 2,2-dimethylbutyl, 2-methylpentyl, 2,2-dimethylpropyl, n-hexyl and the like.

The term "alkoxy" as used herein refers to -$OR_{10}$ wherein $R_{10}$ is a loweralkyl group.

The term "halo" as used herein refers to F, Cl, Br or I.

The term "haloalkyl" as used herein refers to a loweralkyl group in which one or more hydrogen atoms has been replaced with a halogen including, but not limited to, trifluoromethyl, trichloromethyl, difluoromethyl, dichloromethyl, fluoromethyl, chloromethyl, chloroethyl, 2,2-dichloroethyl and the like.

The term "halophenyl" as used herein refers to a phenyl group in which one, two, three, four or five hydrogen atoms have been replaced with a halogen including, but not limited to, chlorophenyl, bromophenyl, fluorophenyl; iodophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3,5-trichlorophenyl, 2,4,6-trichlorophenyl, 2-chloro-4-fluorophenyl, 2-chloro-6-fluorophenyl, 2,4-dichloro-5-fluorophenyl, 2,3-difuorophenyl, 2,4-difuorophenyl, 2,5-difuorophenyl, 2,6-difuorophenyl, 3,4-difuorophenyl, 3,5-difuorophenyl, 2,3,5-trichlorophenyl, 2,4,6-trichlorophenyl, 2,3,4-trifluorophenyl, 2,3,6-trifluorophenyl, 2,4,5-trifluorophenyl, 2,4,6-trifluorophenyl, 3,4,5-trifluorophenyl, 2,3,4,5-tetrafluorophenyl, 2,3,5,6-tetrafluorophenyl, pentafluorophenyl and the like.

Acid addition salts of the compounds of the invention can be derived from reaction of an amine-containing compound of the invention with an inorganic or organic acid. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, malonate, glutarate, malate, mandelate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate.

Examples of acids which may be employed to form acid addition salts include such inorganic acids as hydrochloric acid, sulphuric acid and phosphoric acid and such organic acids as oxalic acid, maleic acid, succinic acid and citric acid, as well as the other acids mentioned above.

The term "substantially pure" as used herein refers to a compound which is contaminated by not more than 10% of any other stereoisomer (enantiomer or diastereomer), preferably by not more than 5% of any other stereoisomer and most preferably by not more than 3% of any other stereoisomer.

As used herein, the terms "S" and "R" configuration are as defined by the IUPAC 1974 Recommendations for Section E, Fundamental Stereochemistry, Pure Appl. Chem. (1976) 45, 13–30.

The following examples will serve to further illustrate the compounds and processes of the invention.

EXAMPLE 1

(L)-N,N-Dibenzylphenylalanine benzyl ester

A solution containing L-phenylalanine (161 kg, 975 moles), potassium carbonate (445 kg, 3220 moles), water (675 L), ethanol (340 L), and benzyl chloride (415 kg, 3275 moles) was heated to 90°+15° C. for 10–24 hours. The reaction mixture was cooled to 60° C. and the lower aqueous layer was removed. Heptane (850 L) and water (385 L) were added to the organics, stirred, and the layers separated. The organics were then washed once with a water/methanol mixture (150 L/150 L). The organics were then stripped to give the desired product as an oil, which was carried on in the next step without purification. IR (neat) 3090, 3050, 3030, 1730, 1495, 1450, 1160 cm$^{-1}$, $^1$H NMR (300 MHz, CDCl$_3$) δ 7.5–7.0 (m, 20H), 5.3 (d, 1 H, J=13.5 Hz), 5.2 (d, 1 H, J=13.5 Hz), 4.0 (d, 2H, J=15 Hz), 3.8 (t, 2H, J=8.4 Hz), 3.6 (d, 2H, J=15 Hz), 3.2 (dd, 1 H, J=8.4, 14.4 Hz), $^{13}$C NMR (300 MHz, CDCl$_3$) δ 172.0, 139.2, 138.0, 135.9, 129.4, 128.6, 128.5, 128.4, 128.2, 128.1, 128.1, 126.9, 126.2, 66.0, 62.3, 54.3, 35.6. [α]$_D$ −79° (C=0.9, DMF).

EXAMPLE 2a

4-S-N,N-Dibenzylamino-3-oxo-5-phenyl-pentanonitrile

A solution containing the product of Example 1 (i.e., benzyl ester) (approx. 0.45 moles) in 520 mL tetrahydrofuran and 420 mL acetonitrile was cooled to −40° C. under nitrogen. A second solution containing sodium amide (48.7 g, 1.25 moles) in 850 mL tetrahydrofuran was cooled to −40° C. To the sodium amide solution was slowly added 75 mL acetonitrile and the resulting solution was stirred at −40° C. for more than 15 minutes. The sodium amide/acetonitrile solution was then slowly added to the benzyl ester solution at −40° C. The combined solution was stirred at −40° C. for one hour and then quenched with 1150 mL of a 25% (w/v) citric acid solution. The resulting slurry was warmed to ambient temperature and the organics separated. The organics were then washed with 350 mL of a 5% (w/v) sodium chloride solution, then diluted with 900 mL heptane. The organics were then washed three times with 900 mL of a 5% (w/v) sodium chloride solution, two times with 900 mL of a 10% methanolic water solution, one time with 900 mL of a 15% methanolic water solution, and then one time with 900 mL of a 20% methanolic water solution. The organics were stripped and the resulting material dissolved into 700 mL of hot ethanol. Upon cooling to room temperature, the desired product precipitated. Filtration gave the desired product in 59% yield from the L-phenylalanine. IR (CHCl$_3$) 3090, 3050, 3030, 2250, 1735, 1600, 1490, 1450, 1370, 1300, 1215 cm$^{-1}$, $^1$H NMR (CDCl$_3$) δ 7.3 (m, 1SH), 3.9 (d, 1 H, J=19.5 Hz), 3.8 (d, 2H, J=13.5 Hz), 3.6 (d, 2H, J=13.5 Hz), 3.5 (dd, 1 H, J=4.0, 10.5 Hz), 3.2 (dd, 1 H, J=10.5, 13.5 Hz), 3.0 (dd, 1 H, J=4.0, 13.5 Hz), 3.0 (d, 1H, J=19.5 Hz), $^{13}$C NMR (300 MHz, CDCl$_3$) δ 197.0, 138.4, 138.0, 129.5, 129.0, 128.8, 128.6, 127.8, 126.4, 68.6, 54.8, 30.0, 28.4. [α]$_D$ −95° (c=0.5, DMF).

EXAMPLE 2b

Alternate preparation of 4-S-N,N-Dibenzylamino-3-oxo-5-phenyl-pentanonitrile

To a flask was charged sodium amide (5.8 g, 134 mmol) under nitrogen followed by 100 mL of methyl t-butyl ether (MTBE). The stirred solution was cooled to 0° C. Acetonitrile (8.6 mL, 165 mmol) was added over 1 minute. This solution was stirred at 5°±5° C. for 30 minutes. A solution of (L)-N,N-dibenzylphenylalanine benzyl ester (25 g, 90% pure, 51.6 mmol) in 125 mL of MTBE was added over 15 minutes and the resulting heterogeneous mixture was stirred at 5°±5° C. until the reaction was complete (approx. 3 hours). The reaction was quenched with 100 mL of 25% w/v aqueous citric acid and warmed to 25° C. before separating the layers. The organics were then washed with 100 mL of H$_2$O. The aqueous layer was separated and the organics filtered and concentrated in vacuo. The residue was crystallized from 50 mL of ethanol to afford 13.8 g of the desired product as a white solid.

EXAMPLE 2c

Alternate preparation of 4-S-N,N-Dibenzylamino-3-oxo-5-phenyl-pentanonitrile

To a solution containing sodium amide (120 kg, 3077 moles), heptane (1194 L), and tetrahydrofuran (590 L) cooled to 0° C., was added a solution containing the product of Example 1 (i.e., benzyl ester) (approx. 975 moles), tetrahydrofuran (290 L), heptane (570 L), and acetonitrile (114 L). The addition was done maintaining the temperature below 5° C. The combined solution was stirred at 0°±5° C. for approx. one hour before quenching with 25% citric acid solution (1540 L) to adjust the pH to 5.0–7.0. The upper organic layer was separated and washed with 25% aqueous sodium chloride (715 kg), treated with activated carbon (2 kg), and stripped. The resulting residue was crystallized from a 55° C. ethanol/water solution (809 kg/404 kg). The solution was cooled to 0° C. prior to crystallizing to give approx. 215 kg of the desired product.

EXAMPLE 3

Alternate preparation of 4-S-N,N-Dibenzylamino-3-oxo-5-phenyl-pentanonitrile

To a 1 liter jacketed reaction flask equipped with thermometer, nitrogen inlet, pressure-equalized addition funnel and mechanical stirrer was charged a solution of potassium t-butoxide (32 g, 0.289 mol, 3.0 equiv) in tetrahydrofuran (350 mL) and cooled to an internal temperature of −10° C. To this was added a solution of the product of Example 1 (i.e, benzyl ester) (42.0 g, 0.0964 mol, 1.0 equiv) in tetrahydrofuran (10 mL) and acetonitrile (15 mL, 0.289 mol, 3.0 equiv) via pressure-equalized addition funnel over a period of 20 minutes. During the addition, the internal temperature increased to −5° C. The reaction (now orange and transparent) mixture stirred an additional 30 min at −10° C. An aliquot removed from the reaction mixture after the addition of the benzyl ester solution was quenched in 10% aqueous citric acid and partitioned between heptane was analyzed by HPLC and revealed no starting material remained and the presence of the desired nitrile in 93% ee in favor of the S isomer, Chiralpak AD column, 1 mL/min,. 10%/-propanol in heptane, monitored @205 nm). The contents of the reactor were allowed to warm to 0° C. over 30 minutes. Citric acid (10% aqueous, 200 mL) was charged followed by Heptane (100 mL) and the reaction contents allowed to warm to 20° C. The aqueous phase was separated and the organic phase was washed with 10% aqueous sodium chloride solution (200 mL) and the aqueous phase separated. The organic phase was concentrated in vacuo using a 45° C. bath. n-Butanol (100 mL) was then charged and distillation in vacuo was conducted until the contents were reduced by approximately 10% by volume. The suspension resulting was allowed to cool to 20° C. with mechanical stirring and held at that temperature for 18 hours. The solid was filtered and dried in vacuo at 45° C. The yield of the first crop was 20.5 g (57%). The material was 98% pure by HPLC.

EXAMPLE 4

2-Amino-5-S-N,N-dibenzylamino-4-oxo-1,6-diphenylhex-2-ene

To a −5° C. solution of the nitrile product of Example 2 (90 Kg, 244 moles) in tetrahydrofuran (288 L), was added benzylmagnesium chloride (378 Kg, 2M in THF, 708 moles). The solution was warmed to ambient temperature and stirred until analysis showed no starting material. The solution was then recooled to 5° C. and slowly transferred to a solution of 15% citric acid (465 kg). Additional tetrahydrofuran (85 L) was used to rinse out the original container and the rinse was added to the citric acid quench container. The organics were separated and washed with 10% sodium chloride (235 kg) and stripped to a solid. The product was stripped again from ethanol (289 L) and then dissolved in 80° C. ethanol (581 L)). After cooling to room temperature and stirring for 12 hours, the resulting product was filtered and dried in a vacuum oven at 30° C. to give approx. 95 kg of the desired product. mp 101°–102° C., IR (CDCl$_3$) 3630, 3500, 3110, 3060, 3030, 2230, 1620, 1595, 1520, 1495, 1450 cm$^{-1}$, $^1$H NMR (300 MHZ, CDCl$_3$) d 9.8 (br s, 1H), 7.2 (m, 20H), 5.1 (s, 1H), 4.9 (br s, 1H), 3.8 (d, 2H, J=14.7 Hz), 3.6 (d, 2H, J=14.7Hz), 3.5 (m, 3H), 3.2 (dd, 1 H, J=7.5, 14.4 Hz), 3.0 (dd, 1 H, J=6.6, 14.4 Hz), $^{13}$C NMR (CDCl$_3$) d 198.0, 162.8, 140.2, 140.1, 136.0, 129.5, 129.3, 128.9, 128.7, 128.1, 128.0, 127.3, 126.7, 125.6, 96.9, 66.5, 54.3, 42.3, 32.4. [α]$_D$ –147° (c=0.5, DMF).

EXAMPLE 5

(2S, 3S, 5S)-5-Amino-2-(dibenzylamino)-3-hydroxy-1,6-diphenyl-hexane

A solution of 2-amino-5-S-N,N-dibenzylamino-4-oxo-1,6-diphenylhex-2-ene (30 g, 65 mmol), methanesulfonic acid (24 g, 248 mmol), ethanol (240 mL), and 4 grams of 5% platinum supported on carbon was pressurized to 250 psi with hydrogen and stirred at 5° C. for 14 hours followed by stirring at 23° C. for 10 hours. The pressure was released and the catalyst removed by filtration over celite. The filtrate was diluted with 1N sodium hydroxide (250 mL) and the product extracted with MTBE (300 mL). The organics were washed with brine (100 mL) and concentrated in vacuo to provide the desired product as a yellow oil: IR (CHCl$_3$) 3510, 3400, 3110, 3060, 3030, 1630, $^1$H NMR (300 MHz, CDCl$_3$) δ 7.2 (m, 20H), 4.1 (d, 2H, J=13.5 Hz), 3.65 (m, 1H), 3.5 (d, 2H, J=13.5 Hz), 3.1 (m, 2H), 2.8 (m, 1H), 2.65 (m, 3H), 1.55 (m, 1H), 1.30 (m, 1H), $^{13}$C NMR (300 MHz, CDCl$_3$) δ 140.8, 140.1, 138.2, 129.4, 129.4, 128.6, 128.4, 128.3, 128.2, 126.8, 126.3, 125.7, 72.0, 63.6, 54.9, 53.3, 46.2, 40.1, 30.2.

EXAMPLE 6

Alternative Preparation of (2S, 3S, 5S)-5-Amino-2-(dibenzylamino)-3-hydroxy-1,6-diphenyl-hexane A solution of 2-amino-5-S-N,N-dibenzylamino-4-oxo-1,6-diphenylhex-2-ene (30 g, 65 mmol), methanesulfonic acid (24 g, 248 mmol), ethanol (240 mL), and 4 grams of 5% platinum supported on Deloxan® AP II was pressurized to 1000 psi with hydrogen and stirred at 0°–5° C. for 15 hours followed by stirring at 23° C. for 32 hours. The pressure was released and the catalyst removed by filtration over celite. The flitrate was diluted with 1N sodium hydroxide (250mL) and the product extracted with ethyl acetate (300 mL). The organics were washed with brine (100 mL) and concentrated in vacuo to provide the desired product.

The foregoing is merely illustrative of the invention and is not intended to limit the invention to the disclosed embodiments. Variations and changes which are obvious to one skilled in the art are intended to be within the scope and nature of the invention which are defined in the appended claims.

What is claimed is:

1. A process for the preparation of the substantially pure compound of the formula:

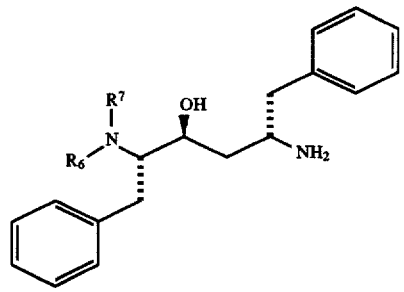

wherein R$_6$ and R$_7$ are independently selected from

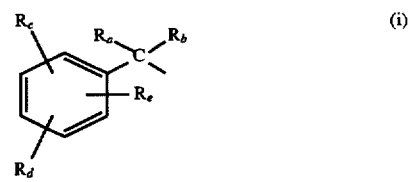

(i)

wherein R$_a$ and R$_b$ are independently selected from hydrogen, loweralkyl and phenyl and R$_c$, R$_d$ and R$_e$ are independently selected from hydrogen, loweralkyl, trifluoromethyl, alkoxy, halo and phenyl; and

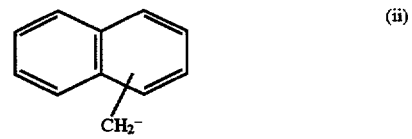

(ii)

wherein the naphthyl ring is unsubstituted or substituted with one, two or three substitutents independently selected from loweralkyl, trifluoromethyl, alkoxy and halo; or R$_6$ and R$_7$ taken together with the nitrogen atom to which they are bonded are

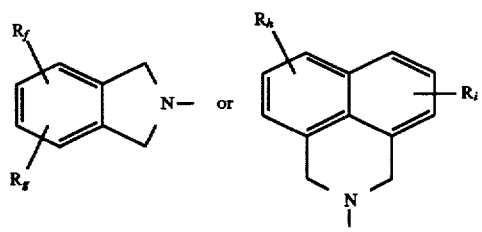

wherein R$_f$, R$_g$, R$_h$ and R$_i$ are independently selected from hydrogen, loweralkyl, alkoxy, halogen and trifluoromethyl; or an acid addition salt thereof, comprising reacting an enaminoketone compound of the formula:

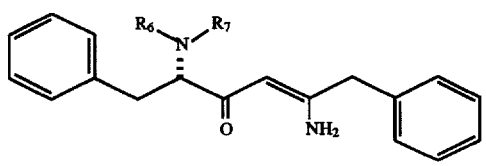

wherein R$_6$ and R$_7$ are defined as above with hydrogen gas in the presence of a hydrogenation catalyst and an acid.

2. The process of claim 1 wherein R$_6$ and R$_7$ are each benzyl or substituted benzyl wherein the phenyl ring of the benzyl group is substituted with one, two or three substituents independently selected from loweralkyl, trifluoromethyl, alkoxy, halo and phenyl.

3. The process of claim 1 wherein the reaction is carried out in a solvent comprising (1) a protic solvent or (2) an ethereal solvent.

4. The process of claim 1 wherein the catalyst is platinum.

5. The process of claim 1 wherein the acid is sulfuric acid or methansulfonic acid.

6. A process for the preparation of the substantially pure compound of the formula:

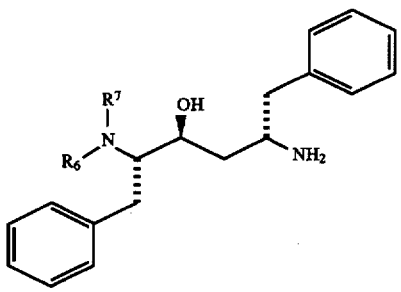

wherein $R_6$ and $R_7$ are independently selected from

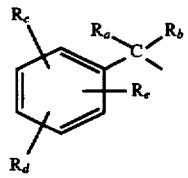 (i)

wherein $R_a$ and $R_b$ are independently selected from hydrogen, loweralkyl and phenyl and $R_c$, $R_d$ and $R_e$ are independently selected from hydrogen, loweralkyl, trifluoromethyl, alkoxy, halo and phenyl; and

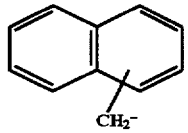 (ii)

wherein the naphthyl ring is unsubstituted or substituted with one, two or three substitutents independently selected from loweralkyl, trifluoromethyl, alkoxy and halo; or $R_6$ and $R_7$ taken together with the nitrogen atom to which they are bonded are

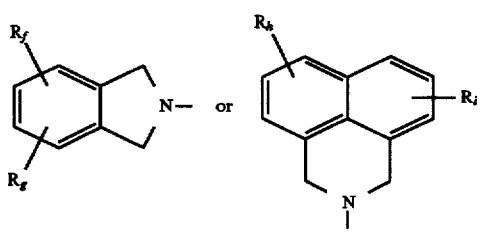

wherein $R_f$, $R_g$, $R_h$ and $R_i$ are independently selected from hydrogen, loweralkyl, alkoxy, halogen and trifluoromethyl; or an acid addition salt thereof, comprising reacting an enaminoketone compound of the formula:

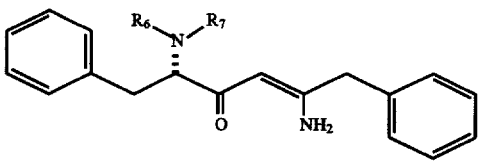

wherein $R_6$ and $R_7$ are defined as above with hydrogen gas in the presence of a hydrogenation catalyst and from about 2 molar equivalents to about 4 molar equivalents (based on the enaminoketone) of an acid.

7. The process of claim 6 wherein $R_6$ and $R_7$ are each benzyl or substituted benzyl wherein the phenyl ring of the benzyl group is substituted with one, two or three substituents independently selected from loweralkyl, trifluoromethyl, alkoxy, halo and phenyl.

8. The process of claim 6 wherein the reaction is carried out in a protic solvent or an ethereal solvent.

9. The process of claim 6 wherein the catalyst is platinum.

10. The process of claim 6 wherein the acid is sulfuric acid or methanesulfonic acid.

11. The process of claim 6 for the preparation of the substantially pure compound of the formula:

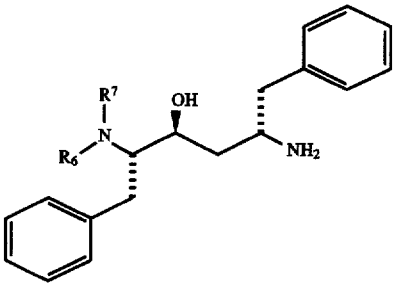

wherein $R_6$ and $R_7$ are independently selected from

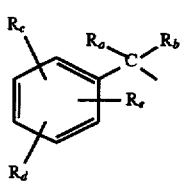

wherein $R_a$ and $R_b$ are independently selected from hydrogen, loweralkyl and phenyl and $R_c$, $R_d$ and $R_e$ are independently selected from hydrogen, loweralkyl, trifluoromethyl, alkoxy, halo and phenyl; or an acid addition salt thereof, comprising reacting an enaminoketone compound of the formula:

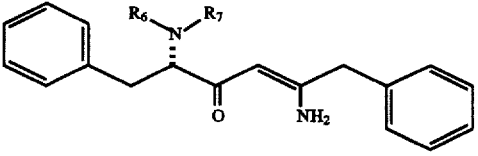

wherein $R_6$ and $R_7$ are defined as above with hydrogen gas in the presence of a hydrogenation catalyst and from about 2 molar equivalents to about 4 molar equivalents (based on the enaminoketone) of an acid.

12. The process of claim 11 for the preparation of the substantially pure compound of the formula:

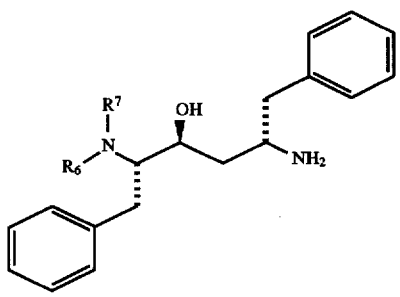

wherein R$_6$ and R$_7$ are each benzyl or an acid addition salt thereof, comprising reacting an enaminoketone compound of the formula:

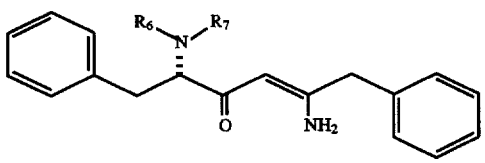

wherein R$_6$ and R$_7$ are defined as above with hydrogen gas in the presence of a hydrogenation catalyst and from about 2 molar equivalents to about 4 molar equivalents (based on the enaminoketone) of an acid.

13. A process for the preparation of the substantially pure compound of the formula:

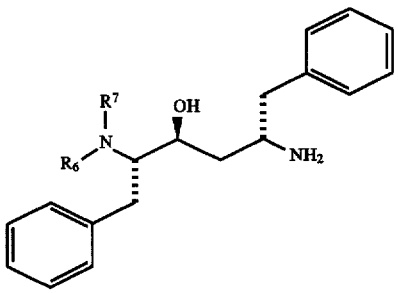

wherein R$_6$ and R$_7$ are each benzyl or an acid addition salt thereof, comprising reacting an alcohol solution of the enaminoketone compound of the formula:

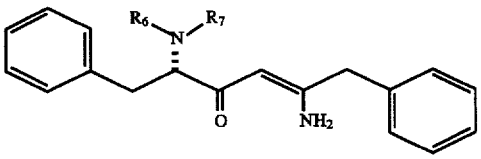

wherein R$_6$ and R$_7$ are defined as above with hydrogen gas at a pressure of from about 60 psi to about 1000 psi in the presence of a platinum catalyst and from about 2 molar equivalents to about 4 molar equivalents (based on the enaminoketone) of methanesulfonic acid.

14. The process of claim 13 wherein the alcohol is ethanol.

15. The process of claim 13 wherein the catalyst is platinum on carbon or platinum on aminopolysiloxane.

* * * * *